United States Patent [19]

Saito

[11] 4,345,341

[45] Aug. 24, 1982

[54] VACUUM SUCTION TYPE URINATING AID

[75] Inventor: Shuichi Saito, Funabashi, Japan

[73] Assignee: Kimura Bed Mfg. Company Limited, Tokyo, Japan

[21] Appl. No.: 179,883

[22] Filed: Aug. 20, 1980

[30] Foreign Application Priority Data

Apr. 25, 1980 [JP] Japan .................. 55-57026
Apr. 25, 1980 [JP] Japan .................. 55-57027

[51] Int. Cl.³ .................. A61F 5/44; A61M 1/00; F01M 1/10
[52] U.S. Cl. .................. 4/301; 4/144.3; 4/305; 128/278; 128/295; 128/760; 181/202; 181/234
[58] Field of Search .................. 4/301, 302, 305, 431, 4/434, 435, 437, 144.1–144.4, 316, 450, 454, 457, 462, 463; 128/276, 278, 295, 760, 762, 765, 766; 181/202, 234, 264, 284, 270, 281

[56] References Cited

U.S. PATENT DOCUMENTS

| 2,749,558 | 6/1956 | Lent et al. | 4/316 X |
| 3,779,341 | 12/1973 | Huggins | 181/264 X |
| 4,084,589 | 4/1978 | Kulic | 128/295 X |
| 4,264,282 | 4/1981 | Crago | 181/202 X |
| 4,281,655 | 8/1981 | Terauchi | 4/305 X |

FOREIGN PATENT DOCUMENTS

| 1521057 | 3/1968 | France | 181/202 |
| 1577688 | 6/1969 | Italy | 181/202 |
| 288661 | 6/1953 | Switzerland | 181/202 |
| 16530 | of 1908 | United Kingdom | 181/281 |

*Primary Examiner*—Stuart S. Levy
*Attorney, Agent, or Firm*—Wenderoth, Lind & Ponack

[57] ABSTRACT

A vacuum suction type urinating aid comprises a urine transport tube connected, at one end, with a urine receiver provided with a urine suction opening to be applied to a urinating region, and connected, at the other end, with a urine tank communicating to a vacuum suction device. The vacuum suction device is provided with a partition and support plate around a motor mounted with an impeller, to fit the motor by the support plate to a casing forming an air passage. The suction and the delivery side of the air passage communicate through the impeller. The casing is internally provided with plural silencing partition plates at the suction side and the delivery side of the air passage to divert the air current passing therethrough.

5 Claims, 7 Drawing Figures

VACUUM SUCTION TYPE URINATING AID

BACKGROUND OF THE INVENTION

The present invention relates to a vacuum suction type urinating aid.

There are people who must be assisted in urinating in bed. These people include the old lying in bed, serious patients, patients suffering from the incontinence of urine, etc. who cannot control their urination as soon as they feel a desire to urinate, and patients who cannot go to the toilet alone.

To attain the objective of assistance, an apparatus in which a receiver applied to the urinating region of the patient to receive his urine is connected with a tank to collect the urine through a tube has been used hitherto. However, with the conventional apparatus, the urine received by the receiver is dropped into the tank through the tube simply by gravity, and therefore the tube and the tank must be placed below the receiver to enable urine to reach the tank by gravity. For example, if the patient changes his position, causing the tube to be placed even partially above the receiver, the urine in the tube flows back into the receiver, to soak the patient and bedclothes inconveniently. Such a conventional apparatus is disadvantageously restricted in the place of use and urinating pose.

SUMMARY OF THE INVENTION

The urinating aid of the present invention receives the urine of the patient in a urine receiver applied to his urinating region, and transports it to a urine tank through a urine transport tube forcedly together with air by vacuum suction, thereby overcoming the disadvantage of the conventional apparatus perfectly. In other words, even when the urine transport tube and the urine tank cannot be placed below said urine receiver, the present invention allows urine to be transported into the urine tank, while preventing any back flow at all.

Thus, the present invention permits a patient to urinate while lying in bed by reasonable application of a vacuum suction device such. However, if an ordinary vacuum suction device as employed for a vacuum cleaner is used, the heavy noise generated will displease the patient himself, his attendant, and others, not only at night but also in the daytime. In view of this, the present invention provides a vacuum suction type urinating aid equipped with a vacuum suction device which generates only a very low noise level.

DETAILED DESCRIPTION OF THE INVENTION

The present invention is described below with detail in reference to the drawings which show preferred embodiments.

Figure 1:
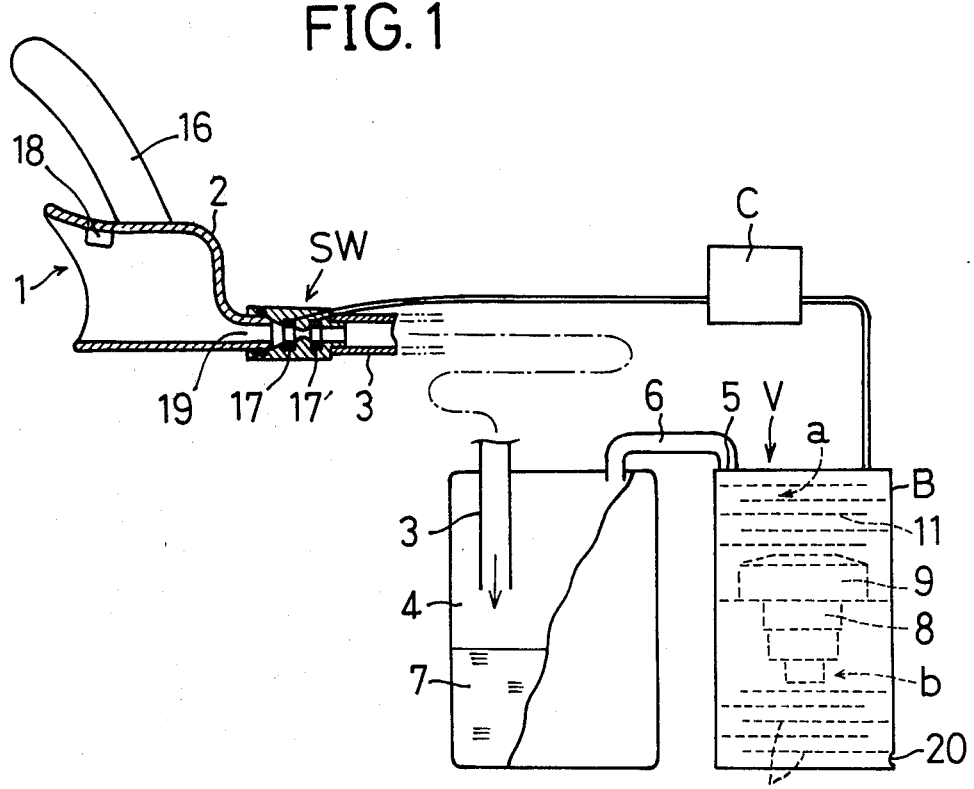
FIG. 1 is a sectional view of a systematic illustration to show an embodiment of the general composition of the vacuum suction type urinating aid of the present invention.
Figure 2:
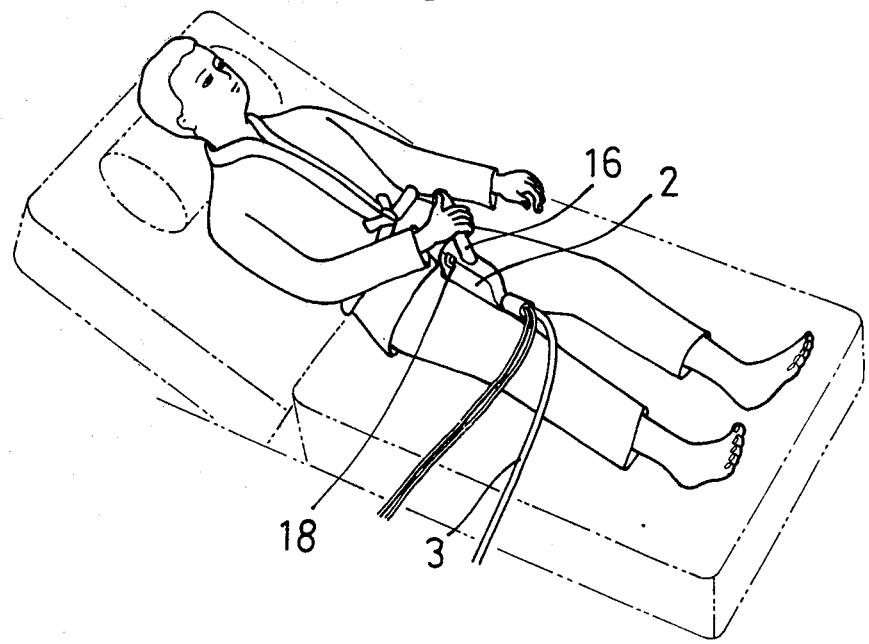
FIG. 2 is an illustrative perspective view of illustrating the manner of use of the vacuum suction type urinating aid of the present invention.
Figure 3:
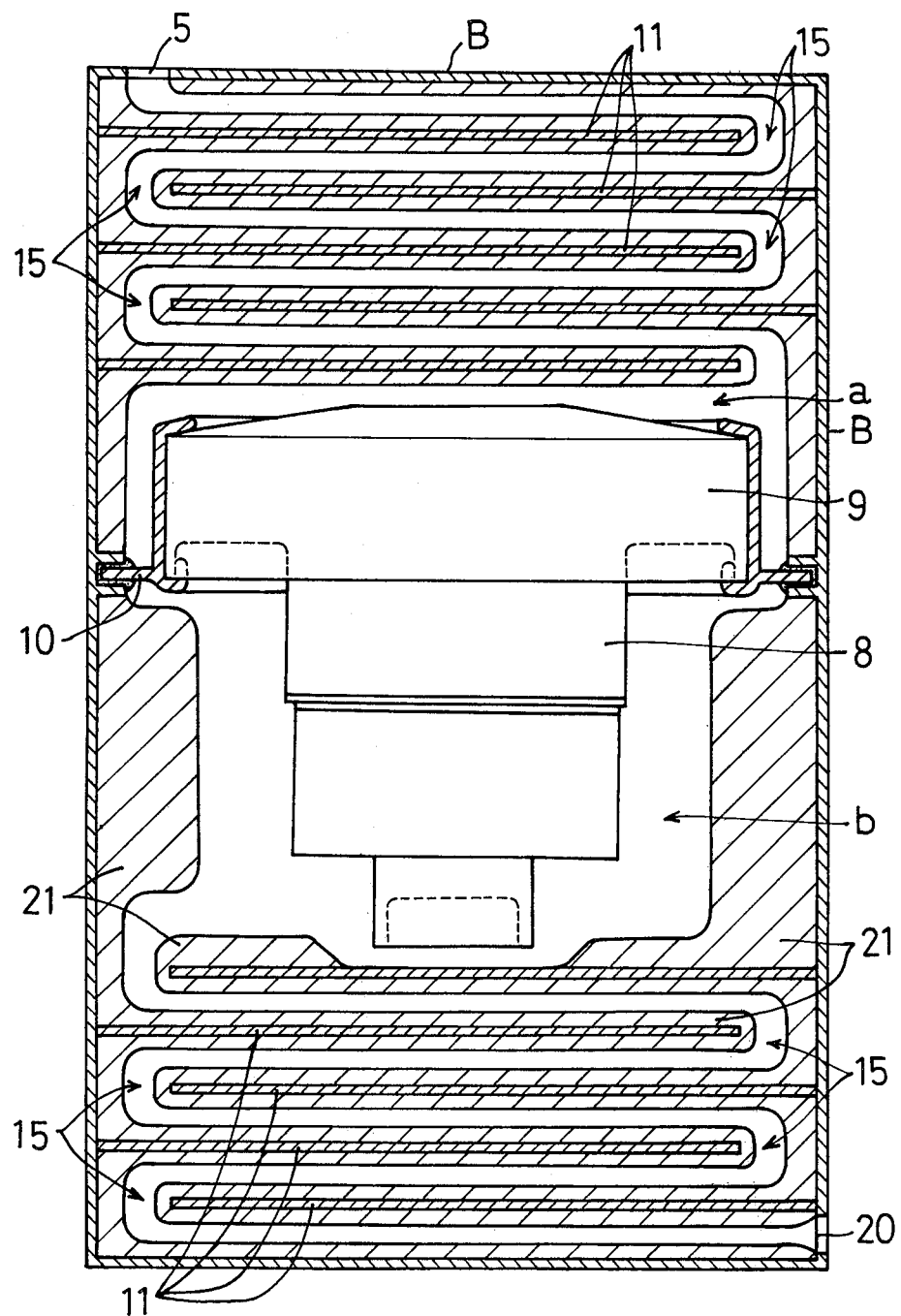
FIG. 3 is an illustrative longitudinal sectional view illustrating a first embodiment of the vacuum suction device of the present invention.
Figure 4:
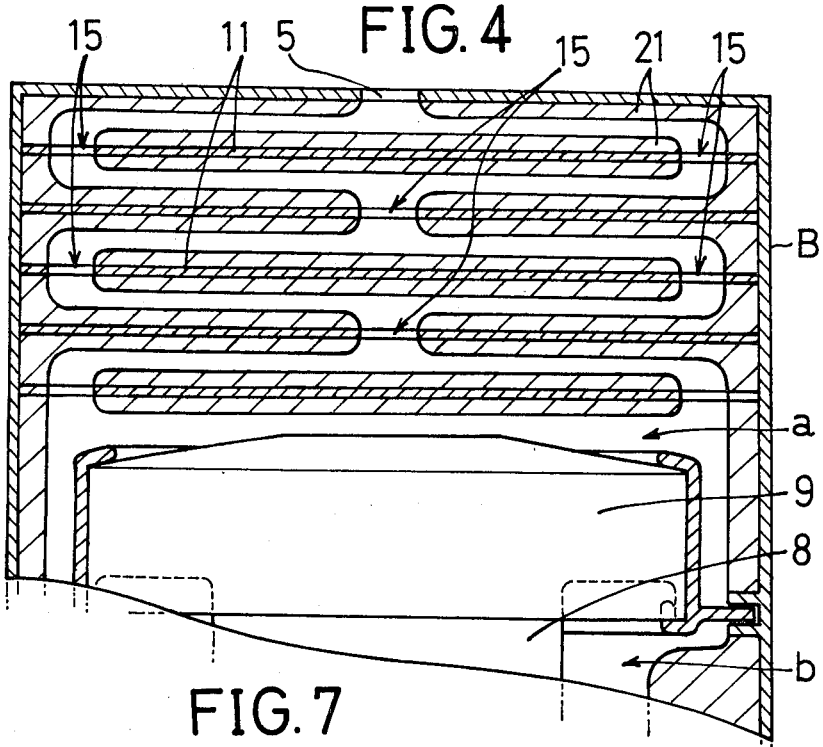
FIG. 4 is an illustrative longitudinal sectional view of a main portion of a vacuum suction device formed by partially changing the first embodiment shown in FIG. 3.
Figure 7:
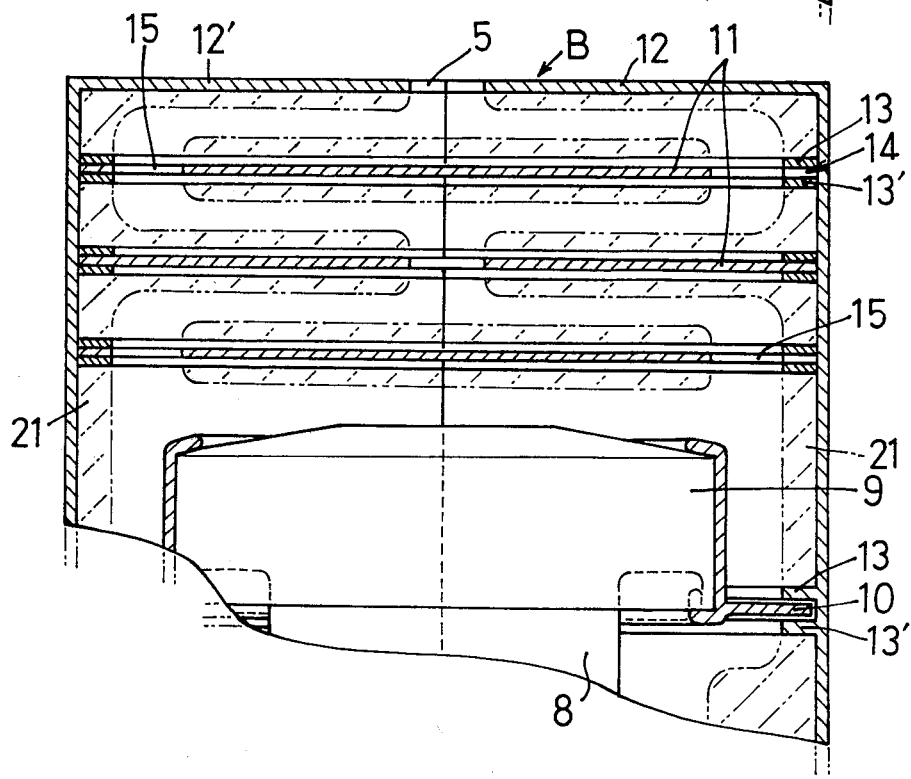
FIG. 7 is an illustrative longitudinal view of a main portion of the vacuum suction device formed by partially changing the second embodiment shown in FIGS. 5 and 6.
Figure 5:
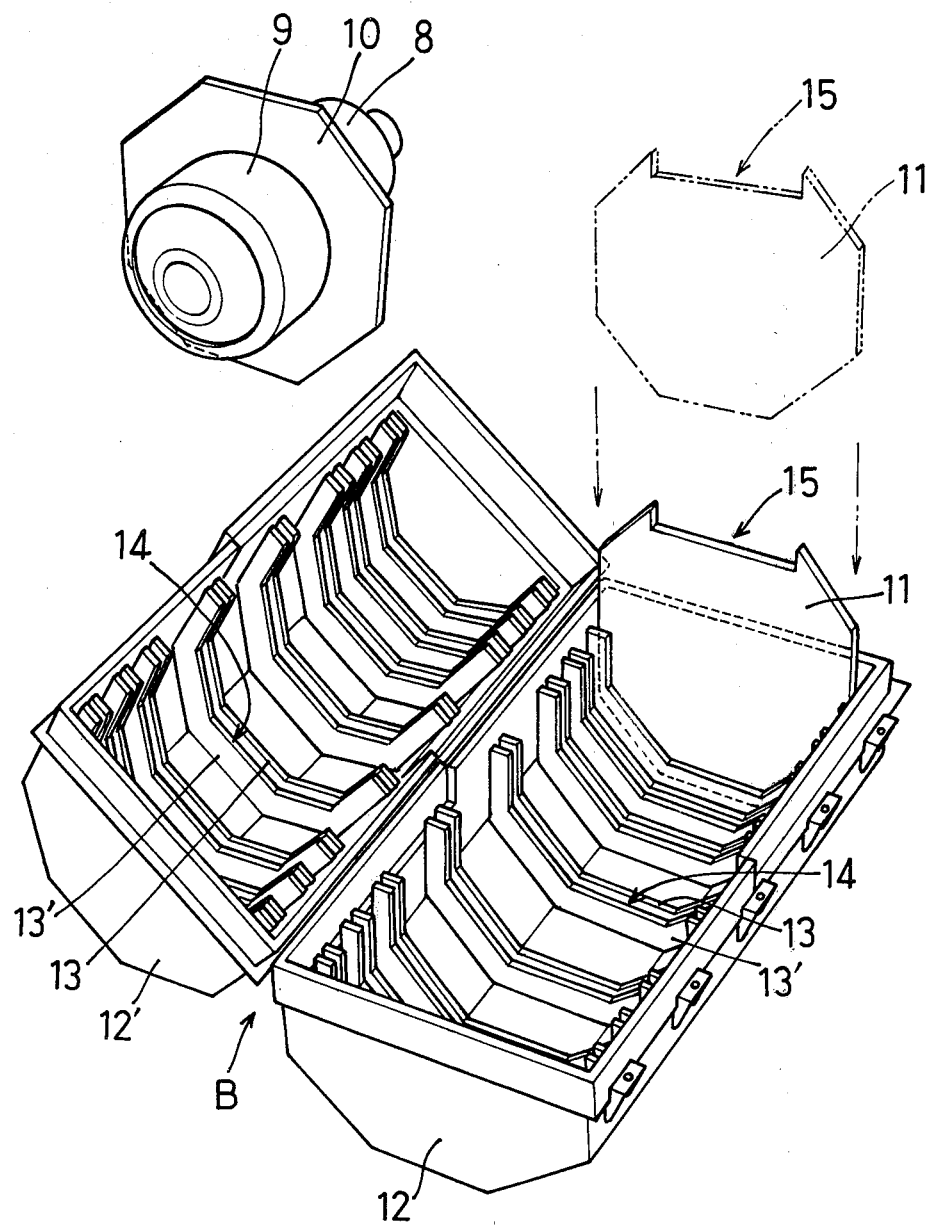
FIG. 5 is an illustrative perspective view illustrating a component of a second embodiment of the vacuum suction device used in the present invention.
Figure 6:
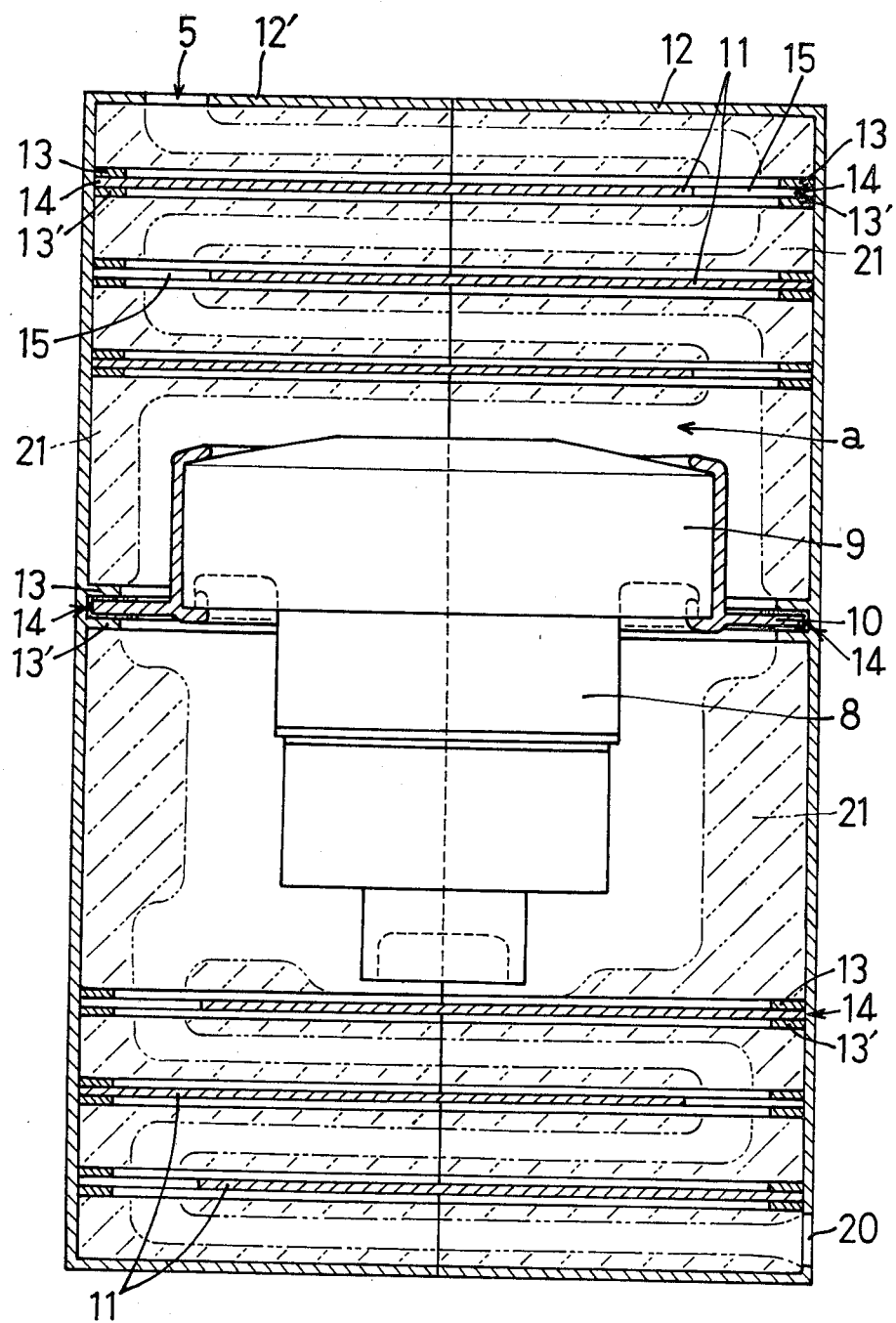
FIG. 6 is an illustrative longitudinal sectional view of the second embodiment.

FIG. 1 shows an embodiment of the general composition of the vacuum suction type urinating aid of the present invention. Such vacuum suction type urinating aid has a urine receiver 2 provided with a urine suction opening 1 at the front side, and a urine transport tube 3 connected, at one end, to the rear side of the urine receiver 2 and connected, at the other end, to a urine tank 4 which is further connected to a vacuum suction device V. The connection of urine tank 4 with a suction port 5 of the vacuum suction device V is made through a vacuum suction tube 6, and vacuum suction tube 6 is connected to the upper part of the urine tank 4, lest the urine 7 in the urine tank should be withdrawn by suction. In the drawings, said urine tank 4 is separated from vacuum suction device V, but they can be of course arranged solidly in a proper housing. Vacuum suction device V is composed as described below. In the drawings, symbol 8 indicates a motor equipped with an impeller 9, and a support plate 10 which is also a partition plate is provided around motor 8. Motor 8 thus is mounted in a casing B forming an air passage by support plate 10. In such air passage, a suction side a and a delivery side b communicate through impeller 9. Casing B is provided with plural silencing partition plates 11 in the suction side a and the delivery side b of the air passage, to divert an air current. In the first embodiment, silencing partition plates 11 are formed solidly with the casing B by welding, solid forming or any other proper method. On the contrary, the second embodiment is formed as described below. Symbol B is a casing in which the motor 8 is mounted, as mentioned before, but casing B is formed by combining a pair of casing or shell halves 12 and 12' divided in the longitudinal direction. Shell halves 12 and 12' can be combined by screwing, proper clamps, or any other known method. Shell halves 12 and 12' are respectively provided with fitting grooves 14, each formed by a pair of protrusions 13' on the respective inside wall. The grooves and protrusions extend in the transverse direction of casing B and are spaced in the longitudinal direction thereof. In this composition, as shown in FIG. 5, the support plate 10 of the motor 8 and the plural silencing partition plates 11 are fitted in fitting grooves 14 of shell half 12, and the other shell half 12' is combined to receive the support plate 10 and the plural silencing partition plate 11 in its fitting grooves 14. Thus, the motor 8 and the silencing partition plates 11 can be fixed in the casing B. In this case, the fixing can be intensified by applying a bonding agent between support plate 10 and silencing partition plates 11 on one hand and fitting grooves 14 on the other, or elastic members such as springs or flexible members of a material such as soft resin may be used, to intensify fixing by elastic deformation. In FIG. 5, partition plates 11 and fitting grooves 14 to receive the partition plates 11 are octagonal, but the form can be selected freely. For example, if they are made circular, any slight circumferential deviation which may be caused when fitting into fitting grooves 14 does not prevent the combining of shell halves 12 and 12'. This makes it possible shorten the time required for manufacture, without lowering the silencing effect. Since silencing partition plates 11 are provided to divert an air current, air through openings or portions 15 of the respective adjacent partition plates 11 are formed at positions apart from each other in the transverse direction of the casing B. Portions 15 can be located alternately at both sides around partition plates 11 as shown in FIGS. 3 and 6, or alternately at the center of partition plates 11 and at the peripherally opposite ends as shown in FIGS. 4 and 7, as long as the alternate locations are distant. Moreover, the air through portions 15 can be formed in any other proper way as long as they divert the air current.

In the above composition, the urinating aid of the present invention is operated as described below. When a patient feels a desire to urinate, he applies the urine suction opening 1 of the urine receiver 2 to his urinating region, to urinate into urine receiver 2. Immediately before or after this action, for example, a manual switch (not illustrated) on a handle 16, properly provided at urine receiver 2, is turned on, or for example, the resistance value between a pair of electrodes 17 and 17' provided in the passage of urine is lowered by the urine, to automatically turn on a switch SW, etc., for operating a proper control circuit C, thereby starting the motor 8 of the vacuum suction device V. Then, if the impeller 9 is rotated by the rotation of said motor 8, vacuum pressure is applied through the suction port 5, the vacuum suction tube 6 and the urine tank 4, to the urine transport tube 3. Thus, the urine received through urine suction opening 1 by the urine receiver 2 is sucked forcedly from a urine outlet 19 together with and by the air sucked into urine receiver 2 from the clearance between the urine suction opening 1 and the urinating region and/or from an air suction hole 18 properly provided in urine receiver 2, and is transported into the urine tank 4. The urine drops by gravity to be collected in the urine tank 4, and the air, having transported the urine, is delivered through the vacuum suction tube 6 connected to the top of urine tank 4 and the vacuum suction device V, into open air.

The vacuum suction type urinating aid of the present invention has the important feature that even if the urine transport tube 3 and the urine tank 4 are located above urine receiver 2, urine does not flow back, since the urine received by the urine receiver 2 is forcedly sucked with air by the vacuum suction device V into the urine transport tube 3, and therefore that urinating the aid can be used by serious patients, the old lying in bed, and patients suffering from the incontinence of urine, with no restriction at all in the place of use or urinating pose. If an air suction hole 18 is provided in urine receiver 2 as mentioned above, it prevents the urine suction opening 1 from adhering to the urinating region of the patient, otherwise would be caused by the vacuum pressure, to improve the feeling of using the aid, and even if the urine suction opening 1 is in close contact with the urinating region without any clearance, the volume of air necessary to carry the urine always can be ensured due to the air suction hole 18.

The air separated from urine in the urine tank 4 in this way is fed through the vacuum suction tube 6 connected to the upper part of the urine tank 4, reaching the suction side a in the casing B through the suction port 5, and is delivered through the impeller 9 and the delivery side b into the open air through a delivery port 20. When air passes through the rotating impeller 9, an air sound with a peak at a specific frequency is generated in correspondence with the number of the vanes and the speed of the impeller 9, and the air sound is heard as a loud noise. To cope with this problem, the present invention arranges the plural silencing partition plates 11 in the suction side a and the delivery side b of the air passage, to divert the air current, and the high frequency component of the air sound is attenuated in the diverted passage through silencing partition plates 11 before it reaches suction port 5 and the delivery port 20. In case of sounds of the same sound pressure level, the lower the frequency, the less audible to human ears. Therefore, the vacuum suction device of the present invention can lower the noise level audible to human beings very substantially by use of silencing partition plates 11. In the second embodiment, since the shell halves 12 and 12' have many protrusions 13 and 13' to form the fitting grooves 14 for the silencing partition plates 11 and the support plate 10 of the motor 8, the rigidity of the casing B can be increased by the protrusions 13 and 13'. Therefore, plates 11 can suppress the air sound generated at the portion of impeller 9 and the vibration of the casing B due to an unbalanced moment of the motor described later, and also the leak of such air sound, etc. to the exterior through the wall of the casing B can be prevented. In addition to this feature, the second embodiment has the important features that the casing B can be made at low cost because of simple the fitting of motor 8 and silencing partition plates 11, and that the maintenance of the motor 8 can be made simply, since the casing B for mounting the motor 8 and the impeller 9 is formed by joining the shell halves 12 and 12' divided which are longitudinally. As illustrated, if a sound absorbing material 21 is applied to the inside wall of the casing B and to the silencing partition plates 11 in the first and second embodiments, the air sound can be reduced further effectively. Since silencing can be effected sufficiently even without such sound absorbing material 21, the sound absorbing material 21 may be applied when so required for a particular installation. Furthermore, if the support plate 10 of the motor 8 is made of a material with proper elasticity such as synthetic resin, the vibration caused by the unbalanced moment of the motor 8 can be absorbed, to inhibit the generation of noise caused by such vibration. Therefore, it is effective when the unbalanced moment of the motor 8 used is large.

As described above in detail, the vacuum suction type urinating aid of the present invention has a feature that even when the urine transport tube and the urine tank cannot be placed below the urine receiver, urine can be collected perfectly in the urine tank without causing the urine to flow back, and therefore that a patient can urinate while lying in bed, with no restriction on the place of use or urinating pose, since the urine received by the urine receiver applied to the urinating region of the patient is transported forcedly together with air in the urine transport tube by vacuum suction to the urine tank. Furthermore, the vacuum suction device of the vacuum suction type urinating aid of the present invention has the important feature that the patient himself, his attendant or other patients in the same room are not displeased by its use not only in the daytime but also at night, since the noise level audible to human ears can be lowered very substantially. Thus, the present invention enables such people to urinate, using the aid in bed when necessary, as the old lying in bed, serious patients, patients suffering from the incontinence of urine, etc. who cannot control their urination as soon as they feel a desire to urinate, and patients who cannot go the toilet alone, irrespective of whether they live in private houses or hospitals. The quality of nursing for such patients thus can be improved remarkably.

What is claimed is:

1. A vacuum suction type urinating aid comprising:
   a urine receiver having a urine suction opening adapted to be applied to the urinating region of a subject to receive therefrom urine and a urine outlet;
   a urine tank;
   a urine transport tube connected between said urine outlet and said urine tank; and
   vacuum suction device means connected to said urine tank for creating a vacuum to form an air current drawing any urine in said urine receiver through said urine transport tube into said urine tank, said vacuum suction device means comprising:
   a casing having at opposite ends thereof an inlet connected to said urine tank for receiving said air current and an outlet for discharging said air current;
   said casing being formed by two casing halves divided longitudinally of said opposite ends;
   each said casing half having formed internally thereof a plurality of transversely extending, longitudinally spaced grooves, each said groove being defined by a pair of transversely extending, longitudinally spaced protrusions extending inwardly from the respective said casing half;
   a suction motor including an impeller for creating said air current;
   a partition and support plate supporting said motor, said partition and support plate fitting within respective said grooves in said casing halves with said casing halves joined together, such that an air passage extends through said casing from said inlet, through said impeller to said outlet;
   a first plurality of silencing partition plates fitting within respective said grooves of said casing halves between said inlet and said impeller;
   a second plurality of silencing partition plates fitting within respective said grooves of said casing halves between said impeller and said outlet; and
   said silencing plates altering the direction of said air passage and diverting the path of said air current through said casing, thereby reducing the level of noise generated from said vacuum suction device means.

2. A vacuum suction type urinating aid as claimed in claim 1, further comprising sound absorbing material applied to the inside walls of said casing halves and to said silencing partition plates.

3. A vacuum suction type urinating aid as claimed in claim 1, wherein said partition and support plate is formed of an elastic material.

4. A vacuum suction type urinating aid as claimed in claim 1, wherein adjacent said silencing partition plates define therebetween substantially transversely extending portions of said air passage, and each said silencing partition plate has therethrough at least one opening connecting adjacent transversely extending portions of said air passage.

5. A vacuum suction type urinating aid as claimed in claim 4, wherein said openings in adjacent said silencing partitioning plates are transversely spaced.

* * * * *